(12) United States Patent
Hayakawa et al.

(10) Patent No.: US 7,304,120 B2
(45) Date of Patent: Dec. 4, 2007

(54) EPOXY COMPOUND, PREPARATION METHOD THEREOF, AND USE THEREOF

(75) Inventors: Atsuhito Hayakawa, Yokkaichi (JP); Akihiro Itou, Yokkaichi (JP)

(73) Assignee: Japan Epoxy Resins Co., Ltd., Tokyo (JP)

( * ) Notice: Subject to any disclaimer, the term of this patent is extended or adjusted under 35 U.S.C. 154(b) by 0 days.

(21) Appl. No.: 11/698,184

(22) Filed: Jan. 26, 2007

(65) Prior Publication Data

US 2007/0123684 A1 May 31, 2007

Related U.S. Application Data

(62) Division of application No. 10/927,617, filed on Aug. 27, 2004.

(30) Foreign Application Priority Data

Sep. 26, 2003 (JP) ............................. 2003-335204
Oct. 10, 2003 (JP) ............................. 2003-352233

(51) Int. Cl.
C07D 301/28 (2006.01)
C08G 59/06 (2006.01)
C08K 3/36 (2006.01)
C08L 63/00 (2006.01)
H01L 23/29 (2006.01)

(52) U.S. Cl. .................. 528/97; 257/793; 523/457; 523/466; 525/481; 525/523; 525/533; 528/122; 528/123; 528/124; 549/517; 549/560

(58) Field of Classification Search .................... None
See application file for complete search history.

(56) References Cited

U.S. PATENT DOCUMENTS 6,239,245 B1 * 5/2001 Morita et al. .............. 528/15

FOREIGN PATENT DOCUMENTS

| EP | 810249 A2 | * | 12/1997 |
| JP | 54-122263 A | * | 9/1979 |
| JP | 61-47725 A | * | 3/1986 |
| JP | 61-123618 A | * | 6/1986 |
| JP | H03-220186 | | 9/1991 |
| JP | 5-283560 A | * | 10/1993 |
| JP | 7-82343 A | * | 3/1995 |
| JP | 7-53791 A | * | 6/1995 |
| JP | 8-225714 A | * | 9/1996 |
| JP | 9-12674 A | * | 1/1997 |
| JP | 9-216933 A | * | 8/1997 |

(Continued)

OTHER PUBLICATIONS

Derwent accession No. 2000-260019 for Soviet Union Patent No. 1,154,908 A1, Kurchenko et al., Feb. 20, 1999, two pages.*

CAPLUS accession No. 2000:593107 and Derwent accession No. 2000-269021 for Soviet Union Patent No. 1,226,815 A1, Kachurin et al., Feb. 27, 1999, four pages.*

Primary Examiner—Robert Sellers
(74) Attorney, Agent, or Firm—Manabu Kanesaka

(57) ABSTRACT

An epoxy compound, represented by a general formula (I) is obtained by reacting an anthrahydroquinone compound having a following general formula (II) with epihalohydrin.

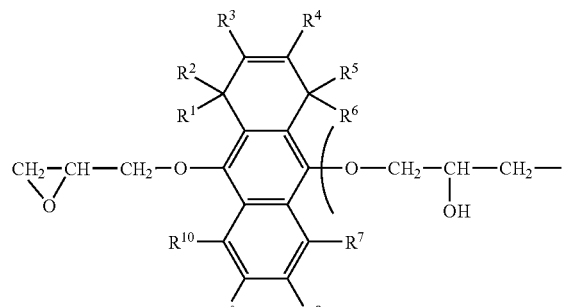

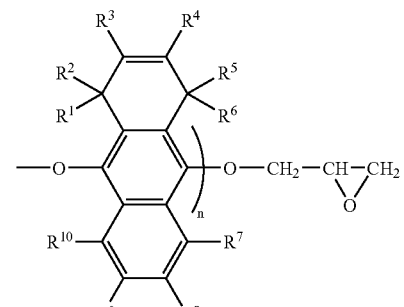

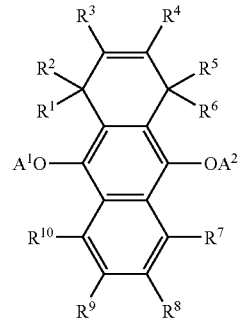

(wherein $R^1$-$R^{10}$ each represent hydrogen atom or alkyl group having 1-6 carbon atoms, and n represents an integer of 0 or more, and wherein $A^1$, $A^2$ each represent hydrogen atom or alkali metal atom, $R^1$-$R^{10}$ each represent hydrogen atom or alkyl group having 1-6 carbon atoms.)

7 Claims, 2 Drawing Sheets

FOREIGN PATENT DOCUMENTS

| | | | | |
|---|---|---|---|---|
| JP | 9-227765 A | * | 9/1997 |
| JP | 9-235449 A | * | 9/1997 |
| JP | 9-241483 A | * | 9/1997 |
| JP | 10-114815 A | * | 5/1998 |
| JP | 10-310629 A | * | 11/1998 |
| JP | 11-158353 A | * | 6/1999 |

* cited by examiner

EPOXY COMPOUND, PREPARATION METHOD THEREOF, AND USE THEREOF

CROSS-REFERENCE TO RELATED APPLICATION

This is a divisional application of Ser. No. 10/927,617 filed on Aug. 27, 2004, allowed.

FIELD OF THE INVENTION

The present invention relates to a novel epoxy compound which is solid at ordinary temperature so as to exhibit excellent handing property and, in its melted state, has extremely low melt viscosity and has excellent curing property and which can provide a cured product which is excellent in mechanical strength, heat resistance, and moisture resistance and to a preparation method of the novel epoxy compound. The present invention also relates to a curable epoxy resin composition containing a novel epoxy compound of the present invention which is useful for applications such as encapsulation material for electric/electronic parts, molding material, cast material, lamination material, composite material, adhesive, and powdered paint, and to a cured product.

The present invention relates to an epoxy resin composition for semiconductor encapsulation which can provide a cured product having superior flame retardance without adding halogen compound and/or antimony compound as a flame retardant component and which has excellent fluidity because it has low viscosity and has excellent crack resistance because it has low hygroscopicity, and to a semiconductor device of which semiconductor elements and/or semiconductor integrated circuits are encapsulated by using the epoxy resin composition.

BACKGROUND OF THE INVENTION

Epoxy compounds are cured with various curing agents to provide cured products which are excellent in mechanical property, moisture resistance, and electrical properties and are thus used in a wide range of fields such as encapsulation material for electric/electronic parts, molding material, cast material, lamination material, composite material, adhesive, and powdered paint. However, as technology advances, the desire for the high performance of epoxy compound grows. Gradually, the desire can not be satisfied by conventional epoxy compounds. For example, with the development of technology of reducing size and thickness of electrical parts in field of electric/electronic applications, epoxy compound is required to have lower viscosity. This is because the resin must flow to sufficiently reach small spaces in a miniaturized part. As epoxy compounds having low viscosity, diglycidy lether of bisphenol A and diglycidy lether of bisphenol F have been widely used. However, since these epoxy compounds are liquid or viscous at ordinary temperature, the workability should be poor because the difficult handing according to the application. Moreover, cured products from these epoxy compounds are not sufficient in mechanical strength, heat resistance, and moisture resistance.

In order to solve these problems, technologies using epoxy compounds which are crystalline at ordinary temperature and over have been proposed. Examples include tetramethylbiphenyl type epoxy compounds (JP-H07-53791-B) and stilbene type epoxy compounds (JP-H09-12674-A). However, these epoxy compounds have high melt viscosity and insufficient curing property because it has bulky substituents near epoxy groups. Though cured products from these epoxy compounds have heat resistance and moisture resistance somewhat better than those of a cured product from the aforementioned bisphenol A-type epoxy compound, these are still insufficient according to specific applications.

The present invention is intended to provide a novel epoxy compound which is solid at ordinary temperature so as to exhibit excellent handing property and, in its melted state, has extremely low melt viscosity and has excellent curing property and which can provide a cured product which is excellent in mechanical strength, heat resistance, and moisture resistance and a preparation method of the novel epoxy compound and further provide a curable epoxy resin composition containing a novel epoxy compound of the present invention which is useful for applications such as encapsulation material for electric/electronic parts, molding material, cast material, lamination material, composite material, adhesive, and powdered paint, and a cured product thereof.

To encapsulate semiconductor elements, epoxy resin compositions are widely used from the viewpoints of reliability, productivity, and cost. These compositions are required to have flame retardance similar to general plastic materials. For this, besides main components, a combination of brominated epoxy resin such as tetrabromobisphenol A type epoxy resin or brominated phenol novolak epoxy resin and an antimony oxide is added as a flame retardant component.

From environmental standpoint, movement toward restriction in use of compounds containing halogen having possibilities of creating dioxin equivalents and use of toxic antimony compound has been increased. Therefore, as for composition for semiconductor encapsulation, technology for achieving flame retardance without using halogen compound such as a brominated epoxy resin and an antimony oxide mentioned above has been gradually studied. For example, as a method of adding a flame retardant alternative to halogen compound and antimony oxide, a method of adding a red phosphorus (JP-H09-227765-A), a method of adding a phosphoric ester compound (JP-H09-235449-A), a method of adding a phosphazene compound (JP-H08-225714-A), and a method of adding a metal hydroxide (JP-H09-241483-A) have been proposed and a method of increasing the adding rate of filler (JP-H07-82343-A) has been also proposed.

However, the method of adding a red phosphorus to prepare an epoxy resin composition for semiconductor encapsulation has a problem of deterioration in moisture resistance reliability and a safety problem due to impact ignitability of the red phosphorus. The method of adding a phosphoric ester compound and the method of adding a phosphazene compound have a problem of deteriorated moldability due to plasticization and a problem of deterioration in moisture resistance reliability. The method of adding a metal hydroxide and the method of increasing the adding rate of filler have a problem of deteriorated fluidity. Any method hasn't been reached to obtain moldability and reliability equivalent to those of the epoxy resin composition for semiconductor encapsulation using brominated epoxy resin with antimony oxide.

On the other hand, in order to cope with complex mounting configuration, the epoxy resin composition is required to have further improved solder crack resistance. To achieve this, it is necessary to sufficiently take care of fluidity of a composition achieving the increased percentage of filler and low hygroscopicity after cured.

To satisfy these requirements, a technology of satisfying both of fluidity and low hygroscopicity by using a composition composed of a tetramethyl biphenol type epoxy resin having low melt viscosity and a phenol resin such as phenol aralkyl resin having nonpolar substituents (JP-S61-47725-A), a technology of mainly using an epoxy resin made of dicyclopentadiene phenol with the bulky substituents for the purpose of improving hygroscopicity (JP-S61-123618-A) have been proposed. However, none of proposal technologies is environment-friendly. These can not achieve sufficient flame retardance without using halogen compound and antimony compound as a flame retardant.

The present invention is intended to provide an epoxy resin composition for semiconductor encapsulation which exhibits excellent flame retardance without using halogen compound and antimony compound as a flame retardant, further exhibits excellent fluidity because of its low viscosity, and is capable of providing a cured product having superior solder crack resistance because of its low hygroscopicity and to provide a semiconductor device of which semiconductor elements are encapsulated by using the aforementioned epoxy resin composition.

SUMMARY OF THE INVENTION

Inventors of the present invention have been dedicated to studying in order to solve the aforementioned problems. As a result, the inventors found that a certain epoxy compound having specific chemical structure is crystal at ordinary temperature so as to maintain its solid state at ordinary temperature, has extremely low viscosity at its melting temperature and over, has excellent curing property, and can provide a cured product which is excellent in mechanical strength, heat resistance, and moisture resistance, thereby having come up with achievement of the present invention.

A first aspect of the present invention provides an epoxy compound having a following general formula (I):

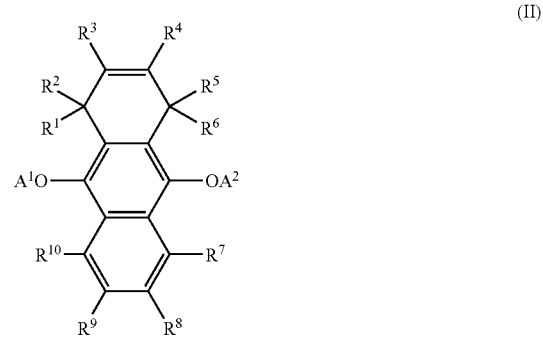

wherein $A^1$, $A^2$ each represent hydrogen atom or alkali metal atom, $R^1$-$R^{10}$ each represent hydrogen atom or alkyl group having 1-6 carbon atoms.

In the method of preparing an epoxy compound, an anthrahydroquinone compound in which $R^1$-$R^{10}$ are hydrogen atoms in the general formula (II) or an anthrahydroquinone compound in which $R^3$, $R^4$ are methyl groups and $R^1$, $R^2$, $R^5$-$R^{10}$ are hydrogen atoms in the general formula (II) may be reacted with epihalohydrin.

Reaction between the anthrahydroquinone compound in which $A^1$, $A^2$ are alkali metals in the general formula (II) and the epihalohydrin for preparing an epoxy compound may be conducted by supplying an aqueous solution of anthrahydroquinone alkali metal salt into a reaction system.

The concentration of anthrahydroquinone alkali metal salt in the aqueous solution of anthrahydroquinone alkali metal salt to be reacted with epihalohydrin may be 5-50% by weight.

In the method of preparing an epoxy compound, 4-40 moles of epihalohydrin is used per one mole of the anthrahydroquinone compound so as to obtain uniform aqueous solution. Into this aqueous solution, 1.8-5 moles of alkali metal hydroxide is added and reacted per one mole of the anthrahydroquinone compound.

A curable epoxy resin composition of a third aspect is a curable epoxy resin composition comprising: an epoxy resin having two or more epoxy groups per molecule; a curing agent; and a curing accelerator, wherein the epoxy resin contains 5-100% by mass of an epoxy compound of the first aspect.

A cured product of a fourth aspect is a cured product made by curing this curable epoxy resin composition.

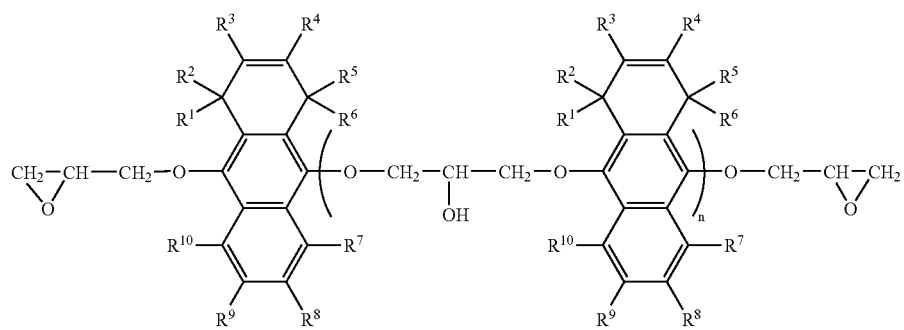

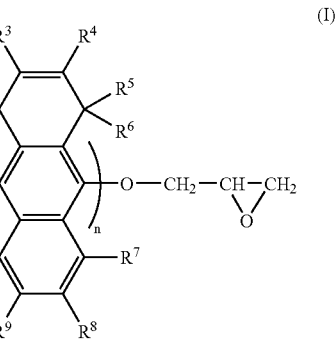

wherein $R^1$-$R^{10}$ each represent hydrogen atom or alkyl group having 1-6 carbon atoms, and n represents an integer of 0 or more.

In the general formula (I), $R^1$-$R^{10}$ may be hydrogen atoms or $R^3$, $R^4$ may be methyl groups while $R^1$, $R^2$, $R^5$-$R^{10}$ are hydrogen atoms.

A second aspect provides a method of preparing an epoxy compound of the first aspect, wherein an anthrahydroquinone compound having a following general formula (II) is reacted with epihalohydrin:

The epoxy compound of the first aspect is crystalline and solid at ordinary temperature so as to have excellent handling property and, in its melted state, has extremely low viscosity. The curable epoxy resin composition of the third aspect prepared by using the epoxy compound has excellent curing property and can provide a cured product which is excellent in mechanical strength, heat resistance, and moisture resistance. Therefore, the epoxy resin composition is useful for applications such as encapsulation material for electric/electronic parts, molding material, cast material, lamination material, composite material, adhesive, and powdered paint.

An epoxy resin composition for semiconductor encapsulation of a fifth aspect is an epoxy resin composition comprising:

an epoxy resin containing 5-100% by mass of an epoxy compound of the first aspect represented by the general formula (I);

a phenolic curing agent having two or more phenolic hydroxyl groups per molecule;

an inorganic filler; and a curing accelerator.

The phenolic curing agent in the epoxy resin composition for semiconductor encapsulation may be at least one phenol resin selected from a group consisting of phenol novolak resin, phenol aralkyl resin, naphthol novolak resin, and naphthol aralkyl resin.

The epoxy resin composition for semiconductor encapsulation may contain, as the inorganic filler, fused and/or crystalline silica powder filler having pulverized form and/or spherical form in an amount of 60-95% by mass of the whole composition.

The epoxy resin composition for semiconductor encapsulation does not contain halogen compound and/or antimony compound as a flame retardant component and a cured product made from the composition may have flame retardance that meets V-0 of UL-94 standard.

The melt viscosity at 150° C. of a mixture in which the epoxy resin in the epoxy resin composition for semiconductor encapsulation and the phenolic curing agent are mixed in equivalent amounts may be 10-200 m Pa·s as a value measured by a cone-plate rotating viscometer.

The epoxy resin composition for semiconductor encapsulation after heated and cured may have a hygroscopic rate which is from 0.1% to 0.5%.

Hygroscopic rate=[(mass of sample piece after process in a temperature- and moisture-controlled chamber at 85° C. and 85% $RH$ for 72 hours−mass of the sample piece before the process)/mass of the sample piece before the process]× 100

A semiconductor device of a sixth aspect is a semiconductor device of which semiconductor elements and/or semiconductor integrated circuits are encapsulated with cured product of an epoxy resin composition for semiconductor encapsulation of the fifth aspect.

The epoxy resin composition for semiconductor encapsulation of the fifth aspect is excellent in flame retardance without adding halogen compound and/or antimony compound as a flame retardant component, is excellent fluidity because it has low viscosity, and has low hygroscopicity. Since the composition can therefore provide a cured product which is excellent in solder crack resistance, the composition is useful as an epoxy resin composition for semiconductor encapsulation. In addition, the semiconductor device of the sixth aspect of which elements are encapsulated using the composition have flame retardance without containing halogen compound and/or antimony compound and can be useful as an environmentally-friendly semiconductor.

DESCRIPTION OF THE PREFERRED EMBODIMENTS

Figure 1:
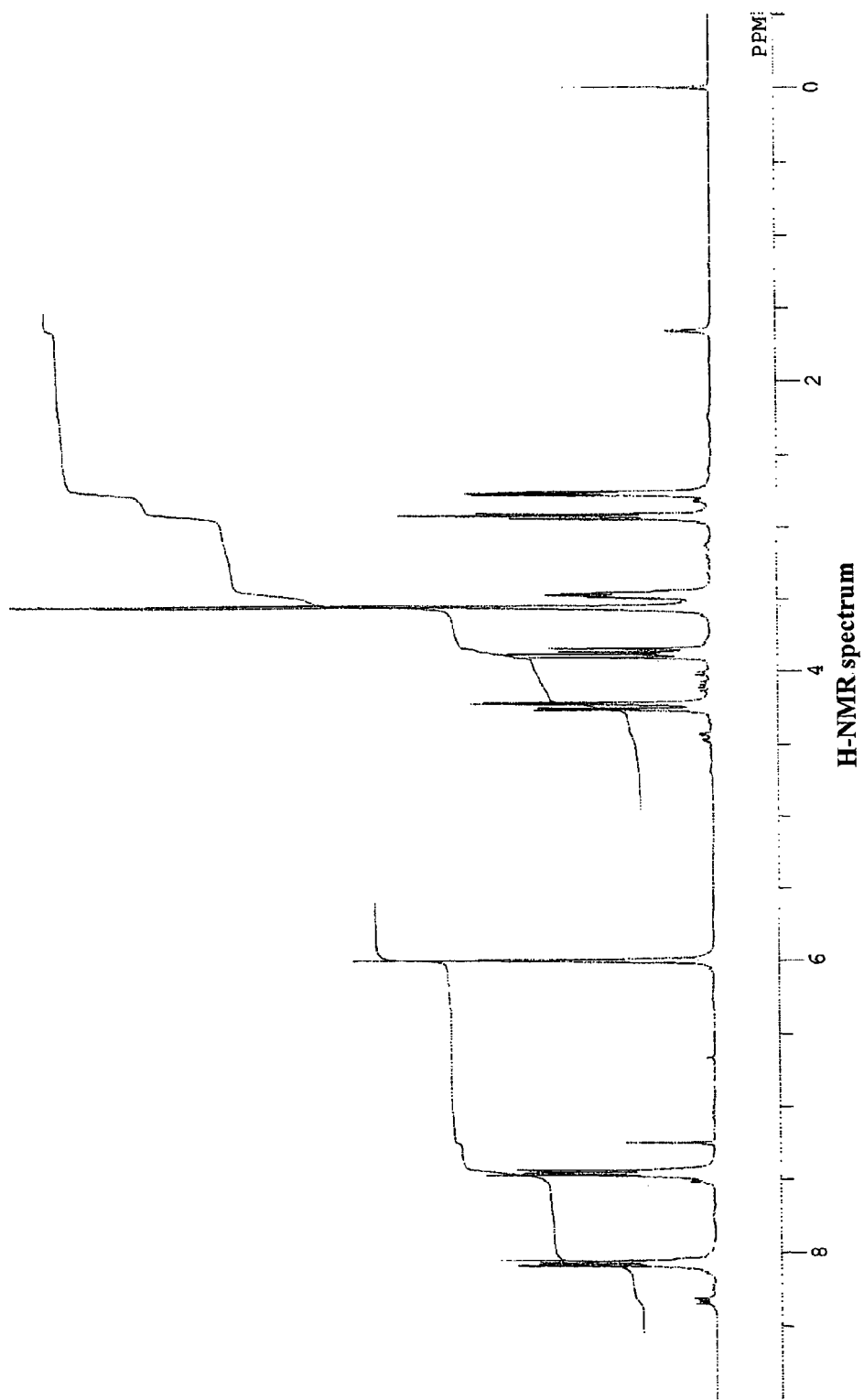
FIG. 1 is a chart showing H-NMR spectrum of an epoxy compound obtained in Example I-1.

[Explanation of Epoxy Compound and its Preparation Method, Curable Epoxy Resin Composition and Cured Product]

The epoxy compound of the present invention represented by the aforementioned general formula (I) is obtained by reacting an anthrahydroquinone compound represented by the aforementioned general formula (II) wherein $A^1$, $A^2$ are hydrogens with epihalohydrin in the presence of alkali metal hydroxide.

For example, anthrahydroquinone compound is solved in epihalohydrin, of which amount is 4-40 moles per one mole of the anthrahydroquinone compound, in the flow of inert gas to have uniform solution. Then, with agitating the solution, alkali metal hydroxide in the form of a solid or an aqueous solution is added into the solution in an amount of 1.8-5 moles per one mole of the anthrahydroquinone compound so as to cause reaction. This reaction can be conducted at normal pressures or under reduced pressures. The reaction temperature is 30-120° C. in case of reaction at normal pressure or 30-80° C. in case of reaction under reduced pressures. During reaction, the reaction liquid is brought to boil with keeping a predetermined temperature as necessary. Condensate liquid is obtained by cooling vapor released from the boiling liquid. The condensate liquid is separated into oil and moisture. The oil after removing the moisture is returned to the reaction system. Dehydration may be conducted in the aforementioned manner. The alkali metal hydroxide is added intermittently or continuously in small amount for 1 to 8 hours in order to prevent sudden reaction. The total reaction time is generally 1 to 10 hours. It is preferable to keep inert gas atmosphere in the reaction system until the reaction terminates. Here, the inert gas means, for example, nitrogen or argon.

In the preparation of the novel epoxy compound of the present invention, the crystalline property and low viscosity property as characteristics of the present invention can be both achieved by controlling the mole ratio of epihalohydrin relative to the anthrahydroquinone compound. The mole ratio of epihalohydrin relative to one mole of the anthrahydroquinone compound is preferably from 4 to 40 moles, more preferably from 8 to 20 moles. If the mole ratio is less than 4, the melt viscosity of the epoxy compound must be high. Even if the mole ratio is higher than 40, the viscosity of the epoxy compound is no more reduced. In addition, the mole ratio higher than 40 is inefficient because it is troublesome to remove unreacted epihalohydrin.

After the reaction, insoluble by-product salt is removed by filtering or water washing. After that, unreacted epihalohydrin is removed under reduced pressures, thereby obtaining a desired epoxy compound.

The epihalohydrin used for this reaction is generally epichlorohydrin or epibromohydrin. The alkali metal hydroxide is generally sodium hydroxide or potassium hydroxide which may be solid (in flake form or powder form) or aqueous of 5-60% by mass. The alkali metal hydroxide may be used as a solution for an organic solvent of polar or nonpolar.

This reaction may use catalysts, for example, quaternary ammonium salts such as tetramethyl ammonium chloride or tetraethyl ammonium bromide; tertiary amine compounds such as benzyldimethylamine or 2,4,6-tris(dimethylaminomethyl) phenol; imidazoles such as 2-ethyl-4-methylimidazole or 2-phenylimidazole; phosphonium salts such as ethyltriphenyl phosphonium iodide; and phosphines such as triphenyl phosphine.

This reaction may also use inert organic solvents, for example, alcohols such as ethanol or 2-propanol; ketones such as acetone or methyl ethyl ketone; ethers such as dioxane or ethylene glycol dimethyl ether; and glycol ethers such as methoxypropanol; aprotic polar solvents such as dimethylsulfoxide or dimethylformamide. These inert organic solvents may be used alone or in combination.

In the case that a saponifiable halogen content in an epoxy compound obtained in the aforementioned manner is too large, the epoxy compound may be re-treated, thereby obtaining a purified epoxy compound having sufficiently decreased saponifiable halogen content. Specifically, the crude epoxy compound is re-dissolved in an inert organic solvent such as 2-propanol, methyl ethyl ketone, methyl isobutyl ketone, toluene, xylene, dioxane, methoxypropanol or dimethylsulfoxide, an alkali metal hydroxide is added to the solution in the form of a solid or an aqueous solution, and re-cyclization reaction is conducted at a temperature of about 30-120° C. for 0.5-8 hours. Thereafter, excess alkali-metal hydroxide or by-product salts are removed by, for example, water washing, and the organic solvent is further removed under reduced pressure, thereby obtaining a purified epoxy compound.

In the aforementioned general formula (I), n is an integer of 0 or more, for example, between 0 and 20. This value can be obtained by controlling the mole ratio of epihalohydrin relative to the anthrahydroquinone compound during the preparation of the epoxy compound. It is preferable that a component in which n=0 is 50% by mole or more. In case that the component in which n=0 is less than 50% by mole, the obtained epoxy compound has not low melt viscosity, not exhibiting the characteristics of the present invention. The average of n obtained by GPC measurement is preferably 0-10, more preferably 0-5, especially preferably 0-2. The average of n is a value calculated by the following equation:

$$[\text{Average value of } n] = \sum_{n=0}^{n}(n+1)a_n/A - 1$$

In the above formula, $a_n$=area % (GPC measurement) of respective peaks of [n=n] and A is obtained from the following equation:

$$A = \sum_{n=0}^{n} a_n$$

To obtain such epoxy compound, the mole ratio of epihalohydrin relative to one mole of the anthrahydroquinone compound for preparing the epoxy compound of the present invention is preferably 4-40 moles, more preferably 8-20 moles. If the mole ratio is less than 4, the melt viscosity of the epoxy resin is high because the component in which n=0 becomes less. Even if the mole ratio is higher than 40, the viscosity of the epoxy resin is no more reduced. In addition, the mole ratio higher than 40 is inefficient because it is troublesome to remove unreacted epihalohydrin.

In addition, an epoxy compound of the present invention can be prepared also by reacting a previously prepared alkali metal salt of anthrahydroquinone compound, preferably an anthrahydroquinone alkali metal salt wherein both $A^1$, $A^2$ in the aforementioned general formula (II) each are alkali metal, preferably $A^1$, $A^2$ each are potassium atom or sodium atom, with epihalohydrin. In this case, anthrahydroquinone alkali metal salt is added into epihalohydrin in the form of a solid or an aqueous solution and is preferably added intermittently in small amount in order to prevent sudden reaction.

In case of supplying an anthrahydroquinone alkali metal salt in the form of an aqueous solution, it is preferable to increase the ratio of epoxidation by adding the alkali metal hydroxide in the form of a solid or an aqueous solution after removing water in the system on the way of reaction in order to sufficiently conduct the cyclization reaction.

The concentration of anthrahydroquinone alkali metal salt in the aqueous solution of anthrahydroquinone alkali metal salt is 5-50% by mass, preferably 15-30% by mass. In case of concentration less than 5% by mass, the amount of water to be brought into the system must be large, inhibiting the process of the epoxidation reaction. In case of concentration more than 50% by mass, the fluidity of the aqueous solution must be poor, leading to blockage of pipes of an apparatus.

In addition, the aqueous solution of anthrahydroquinone alkali metal salt may contain alkali metal hydroxide in an amount required to form salt or more in order to stabilization. Other organic solvent(s) such as alcohols may be added into the aqueous solution if its stability is not damaged.

In case of anthrahydroquinone alkali metal salt or its aqueous solution as starting material, an epoxy compound can be obtained using various conditions, various reaction catalysts, various organic solvents and operations similar to the epoxidation reaction of the aforementioned anthrahydroquinone compound. In addition, the aforementioned method of obtaining purified epoxy compound from crude epoxy compound can also be used.

Since the removal of reaction solvent is normally carried out at a temperature near the melting point of epoxy compound or more, the epoxy compound just after the removal of solvent is in melted state. Method of crystallizing the epoxy compound in melted state to convert the epoxy compound into solid state is not limited. Any known method can be used. Examples include a method of crystallization and solidification by pulling an epoxy compound in melted state onto a tray or the like so that the epoxy compound is naturally cooled, a method of promoting the crystallization of an epoxy compound by adding previously prepared epoxy compound crystals as crystal nucleus after pulling the epoxy compound out, a method of promoting the crystallization of an epoxy compound by agitating or vibrating the epoxy compound in melted state, a method of pulling an epoxy compound with applying strong force with a kneader or the like, and a method of promoting the crystallization with controlling the temperature not to excessively cool the epoxy compound. These methods can be conducted alone or in combination. Also as for the novel epoxy compound of the present invention, it is preferable to promote the crystallization by conducting any of the aforementioned operations from the aspect of productivity.

To improve the low viscosity and high purity of an epoxy compound, a crude epoxy compound obtained by reaction or a purified epoxy compound may be recrystallized by using a suitable solvent.

An anthrahydroquinone compound used in the aforementioned reaction is any one of anthrahydroquinone compounds represented by the aforementioned general formula (II) wherein substitutes $R^1$-$R^{10}$ each are hydrogen atom or alkyl group having 1-6 carbon atoms. Among these, preferably $R^1$-$R^{10}$ are hydrogen atoms or methyl groups. More preferable examples are 1,4-dihydroanthrahydroquinone wherein all of $R^1$-$R^{10}$ are hydrogen atoms, and 1,4-dihydro-2,3-dimethylanthrahydroquinone wherein $R^3$, $R^4$ are methyl groups and $R^1$, $R^2$, $R^5$-$R^{10}$ are hydrogen atoms. Most preferable example is 1,4-dihydroanthrahydroquinone. The thus obtained epoxy compound is crystalline having a melting point of 80-130° C. measured by DSC. The epoxy compound has excellent handling property because it easily melts at a temperature higher than the melting point to have quite low viscosity.

Therefore, the epoxy resin of the present invention is preferably represented by a structural formula (III) below prepared in Examples I-1,3-A, and 3-B as will be described later or by a structural formula (V) below prepared in Example I-2 as will be described later. The average of n is preferably 0-10.

In case of using an anthrahydroquinone alkali metal salt for the reaction, the anthrahydroquinone alkali metal salt is also any one of anthrahydroquinone alkali metal salts represented by the aforementioned general formula (II) wherein substitutes $R^1$-$R^{10}$ each are hydrogen atom or alkyl group having 1-6 carbon atoms. Among these, preferably $R^1$-$R^{10}$ are hydrogen atoms or methyl groups. More preferable examples are an alkali metal salt of 1,4-dihydroanthrahydroquinone wherein all of $R^1$-$R^{10}$ are hydrogen atoms and an alkali metal salt of 1,4-dihydro-2,3-dimethylanthrahydroquinone wherein $R^3$, $R^4$ are methyl groups and $R^1$, $R^2$, $R^5$-$R^{10}$ are hydrogen atoms. Most preferable example is an alkali metal salt of 1,4-dihydroanthrahydroquinone.

Examples of alkali metals capable forming salts are potassium and sodium which are generally supplied as hydroxides (potassium hydroxide and sodium hydroxide) in the natural form or the form dissolved in solvent such as water or alcohol.

The method of preparing an anthrahydroquinone compound as the raw material of the novel epoxy compound of the present invention may be any of known suitable methods. For example, 1,4,4a,9a-tetrahydroanthraquinone obtained by Diels-Alder Reaction between 1,4-naphthoquinone and butadiene is subjected to isomerization reaction by using a aromatic hydrocarbon such as benzene or xylene as a solvent and para-toluenesulfonic acid as a catalyst at a temperature of 80-100° C. for 30 minutes to 3 hours and, after that, is cooled, thereby obtaining crystalline epoxy compounds (JP-S54-122263-A).

Similarly, the method of preparing an anthrahydroquinone alkali metal salt may be any of known suitable methods. Examples are a method of dissolving the anthrahydroquinone compound obtained by the aforementioned method into aqueous solution in which alkali metal hydroxide is dissolved in at least a corresponding amount (twice as mole of anthrahydroquinone compound) and a method of bringing the 1,4,4a, 9a-tetrahydroanthraquinone, obtained by Diels-Alder Reaction between 1,4-naphthoquinone and butadiene, into contact with aqueous solution in which alkali metal hydroxide is dissolved in at least a corresponding amount (twice as mole of 1,4,4a,9a-tetrahydroanthraquinone) so as to cause isomerization reaction of 1,4,4a,9a-tetrahydroanthrahydroquinone, thereby obtaining aqueous solution of anthrahydroquinone alkali metal salt. Moreover, since aqueous solution of 1,4-dihydroanthrahydroquinone disodium salt wherein $R^1$-$R^{10}$ are hydrogen atoms and $A^1$, $A^2$ are sodium atoms in the aforementioned general formula (II) is already widely used in the world for applications as pulping cooking auxiliary agent, aqueous solution of 1,4-dihydroanthrahydroquinone disodium salt may be used without any process.

The curable epoxy resin composition of the present invention comprises, as the essential components, (a) an epoxy resin of which one molecule includes two or more epoxy groups, (b) a curing agent, and (c) a curing accelerator and is characterized in that the epoxy resin (a) contains the novel epoxy compound of the present invention. Other than the novel epoxy compound of the present invention, an epoxy resin of which one molecule contains two or more epoxy groups can be compounded in the epoxy resin (a). The epoxy resin can be any of known suitable epoxy resins. Examples include epoxy resins of bisphenol A type, bisphenol F type, biphenyl type, tetramethylbiphenyl type, cresol novolak type, phenol novolak type, bisphenol A novolak type, epoxy resins obtained by condensation reaction of dicyclopentadiene phenol and phenol aralkyl, alicyclic epoxy resin, and aliphatic epoxy resin. These epoxy resins can be used alone or in mixed state of two or more. The proportion of the epoxy compound of the present invention is 5-100% by mass of the whole epoxy resin. If the proportion of the epoxy compound of the present invention is less than 5% by mass, characteristics of the present invention are not sufficiently exhibited.

The curing agent (b) is not particularly specified and may be any of known suitable curing agents. Examples of the curing agent include various polyhydric phenols, such as bisphenol A, bisphenol F, bisphenol S, thiodiphenol, hydroquinone, resorcin, biphenol, tetramethylbiphenol, dihydroxynaphthalene, and dihydroxydiphenyl ether; various phenolic resins such as phenol novolak resin, cresol novolak resin, bisphenol A novolak resin, naphthol novolak resin, phenolic resins obtained by condensation reaction of various phenols and various aldehydes such as benzaldehyde, hydroxybenzaldehyde, methylthiobenzaldehyde, crotonaldehyde or glyoxal, phenol aralkyl resin, phenol denatured xylene resin, phenol terpene resin, and dicyclopentadiene phenolic resin; activated ester compound obtained by converting all or a part of phenolic hydroxyl groups of various phenols (resins) into ester such as benzoate or acetate; acid anhydrides such as methyltetrahydrophthalic anhydride, hexahydrophthalic anhydride, pyromellitic anhydride and methylnadic acid; and amines such as diethylene triamine, isophorone diamine, diaminodiphenyl methane, diaminodiphenyl sulfone and dicyandiamide. These curing agents may be used alone or in combination.

The amount of the curing agent (b) is preferably such an amount that the moles of groups reacting epoxy groups in the entire curing agent is 0.5-2.0, more preferably 0.7-1.2 relative to one mole of epoxy groups in all components of the epoxy resin (a).

The curing accelerator (c) is not particularly specified and may be any of known suitable curing accelerators. Examples of the curing accelerator include phosphine compounds such as tributylphosphine, triphenylphosphine, tris(dimethoxyphenyl)phosphine, tris(hydroxypropyl)phosphine, tris(cyanoethyl)phosphine; phosphonium salts such as tetraphenylphosphonium tetraphenylborate, methyltributylphosphonium tetraphenylborate, methyltricyanoethylphosphonium tetraphenylborate; triphenylphosphine-benzoquinone adducts; imidazoles such as 2-methyl imidazole, 2-phenyl imidazole, 2-ethyl-4-methyl imidazole, 2-undecyl imidazole, 1-cyanoethyl-2-methyl imidazole, 2,4-dicyano-6-[2-methylimidazolyl-(1)]-ethyl-s-triazine and 2,4-dicyano-6-[2-undecylimidazolyl-(1)]-ethyl-s-triazine; imidazolium salts such as 1-cyanoethyl-2-undecylimidazolium trimellitate, 2-methylimidazolium isocyanurate, 2-ethyl-4-methylimidazolium tetraphenylborate and 2-ethyl-1,4-dimethylimidazolium tetraphenylborate; amines such as 2,4,6-tris(dimethylaminomethyl)phenol, benzyl dimethylamine, tetramethylbutyl guanidine, N-methylpiperazine and 2-dimethylamino-1-pyrroline; ammonium salts such as triethylammonium tetraphenylborate; diazabicyclo compounds such as 11,5-diazabicyclo[5,4,0]-7-undecene, 1,5-diazabicyclo[4,3,0]-5-nonene and 1,4-diazabicyclo[2,2,2]-octane; and tetraphenylborates, phenol salts, phenol novolak salts and 2-ethylhexanoates of these diazabicyclo compounds. Among the compounds as curing accelerators, phosphine compounds, imidazole compounds, diazabicyclo compounds, and salts of these are preferable. These compounds as curing accelerators can be used alone or in mixed state of two or more. The proportion of the curing accelerator (c) is 0.1-7% by mass relative to the whole components of the epoxy resin (a).

If necessary, filler, coupling agent, flame retardant, flame retardant aid, plasticizer, solvent, reactive diluent, pigment, and the like can appropriately be compounded in the curable epoxy resin composition of the present invention.

The curable epoxy resin composition of the present invention is a composition in which all components including the epoxy resin (a), the curing agent (b), and the curing accelerator (c) are uniformly mixed by a method similar to any of conventionally known methods. Examples of such methods are the kneading method in melted state using a kneader, a roll, or an extruder and the dry blending method of mixing components in granular form. Thus obtained composition may be pulverized and/or classified, if necessary.

The curable epoxy resin composition of the present invention may be dissolved in a solvent such as acetone, methyl ethyl ketone, methyl cellosolve, dimethyl formamide, toluene, or xylene so as to form varnish-like composition. The varnish-like composition is impregnated in a substrate such as glass fibers, carbon fibers, polyester fibers, polyamide fibers or paper and is heated and dried so as to form a prepreg. This prepreg is pressed into a shape with heat, thereby obtaining a cured product.

The cured product of the present invention can be obtained by curing the curable epoxy resin composition with heat and can have a form such as a molded article, a lamination, a cast article, adhesive, coating, or a film. For example, in case of the form of a molded article, the composition is heated at a temperature of 30-250° C. for 30 seconds to 10 hours using a cast mold, a transfer molding machine, an injection molding machine, thereby obtaining a cured product. In case of the varnish-like form, the composition is impregnated in a substrate such as glass fibers, carbon fibers, polyester fibers, polyamide fibers or paper and is heated and dried so as to form a prepreg. This prepreg is pressed into a shape with heat, thereby obtaining a cured product.

As described in the above, a novel epoxy compound of the present invention is solid at ordinary temperature so as to exhibit excellent handing property and, in its melted state, has extremely low melt viscosity and has excellent curing property. In addition, a curable epoxy resin composition prepared by using the epoxy compound can provide a cured product which is excellent in mechanical strength, heat resistance, and moisture resistance. Therefore, the epoxy resin composition is useful for applications such as encapsulation material for electric/electronic parts, molding material, cast material, lamination material, composite material, adhesive, and powdered paint.

Hereinafter, examples of the epoxy compound and its preparing method and examples of the curable epoxy resin composition and its cured product will be described in detail. However, the present invention is not limited to these examples without departing from the scope of the invention.

EXAMPLE I-1

1050 g of epichlorohydrin and 410 g of 2-propernol were charged into a four-necked flask of 3 liters capacity equipped with a stirrer, a reflux cooling pipe and a thermometer. A system was vacuumed and was replaced by nitrogen. Under the nitrogen atmosphere, 200 g of 1,4-dihydroanthrahydroquinone was added thereto and temperature was elevated to 40° C. to dissolve them uniformly. After that, 180 g of 48.5 mass % aqueous sodium hydroxide solution was added dropwise over 90 minutes. During the addition, temperature was gradually elevated such that the temperature in the system reached 65° C. at the time of completion of the addition.

Thereafter, the system was maintained at 65° C. for 30 minutes to complete reaction. After completion of the reaction, the reaction mixture was washed with water to remove by-product salts and excess sodium hydroxide. Excess epichlorohydrin and 2-propanol were distilled off under reduced pressure from the product to obtain a crude epoxy resin mixture.

This rough epoxy resin mixture was dissolved in 460 g of methyl isobutyl ketone, and 7 g of 48.5 mass % aqueous sodium hydroxide solution was added thereto to conduct reaction at a temperature of 65° C. for 1 hour. After that, aqueous sodium primary phosphate solution was added to the reaction liquid to neutralize excess sodium hydroxide, followed by water washing to remove by-product salts. During water washing, the temperature of the liquid was kept at temperature from 65° C. to 90° C. by temperature control. After methyl isobutyl ketone was completely removed under increased temperature and reduced pressure, resin matter in melted state was pulled onto a tray and stirred dozen times by a glass stick and, after that, was naturally cooled at room temperature. After a lapse of 2 hours, entire crystallization was experienced. The crystallized matter was taken out, thereby obtaining 285 g of yellow crystallized epoxy compound. The obtained epoxy compound had an epoxy equivalent of 176 g/eq, hydrolysable chlorine of 450 ppm, and a melt viscosity of 16 m Pa·s at a temperature of 150° C., and a melting point of 104° C. according to DSC measurement.

Figure 2:
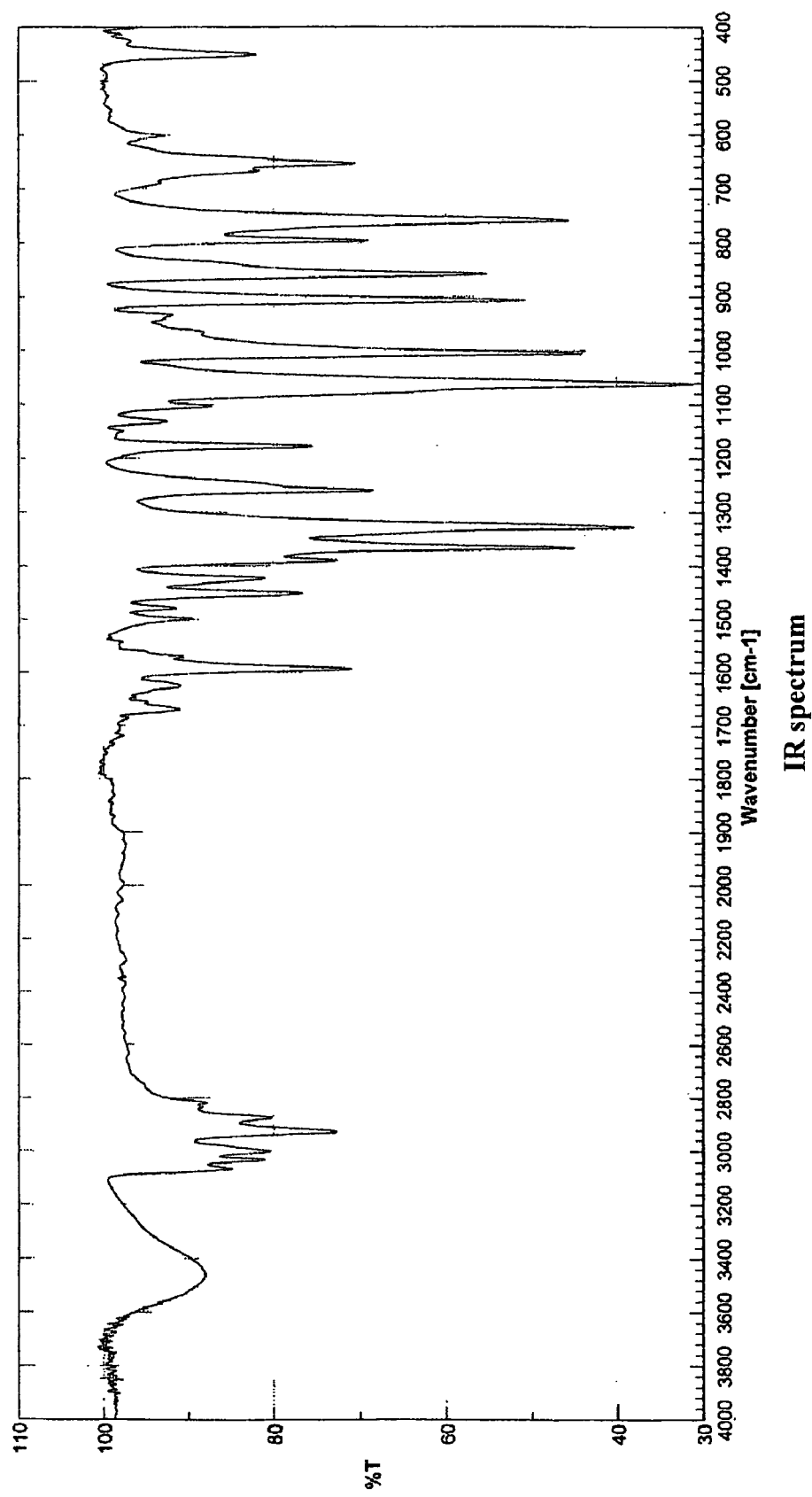
FIG. 2 is a chart showing IR spectrum of the epoxy compound obtained in Example I-1.

The obtained epoxy compound was solid at room temperature so as to have good handling property. H-NMR spectrum of the obtained epoxy compound is shown in FIG. 1 and assignments of respective peaks are shown in Table 1. In addition, IR spectrum of the obtained epoxy compound was shown in FIG. 2.

In the aforementioned manner, it was confirmed that an epoxy compound represented by the following structural formula (III) was obtained. According to GPC, the epoxy compound was a mixture containing 80 mole % of component in which n=0, 17 mole % of component in which n=1, and 3 mole % of component in which n=2 or more, wherein the average of n was 0.21.

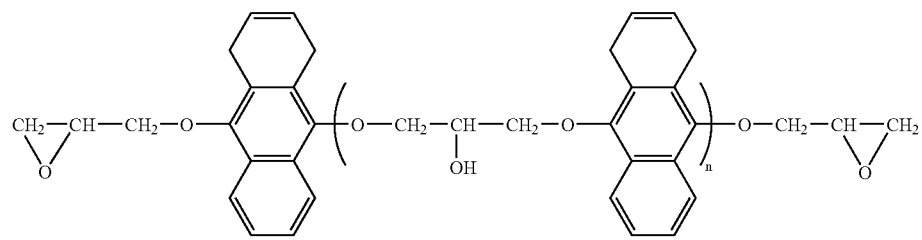

(III)

TABLE 1

| Chemical Shift (ppm) | Assigned hydrogen (formula V) |
|---|---|
| 2.8-2.9 | Ha |
| 3.4-3.50 | Hb |
| 3.56 | Hd |
| 3.8-4.3 | Hc |
| 6.0 | He |
| 7.4-7.5 | Hf |
| 8.0-8.1 | Hg |

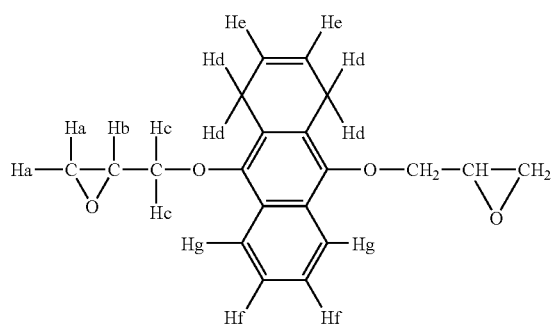

(IV)

EXAMPLE I-2

The same operation as Example I-1 was conducted except using 225 g of 1,4-dihydro-2,3-dimethylanthrahydroquinone instead of 200 g of 1,4-dihydroanthrahydroquinone in Example I-1, thereby obtaining 306 g of epoxy compound represented by the following structural formula (V).

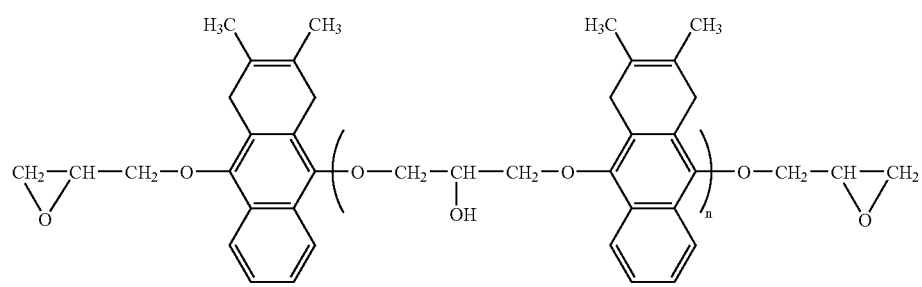

(V)

The obtained epoxy compound had an epoxy equivalent of 194 g/eq, hydrolysable chlorine of 435 ppm, and a melt viscosity of 17 m Pa·s at a temperature of 150° C., and a melting point of 94° C. according to DSC measurement.

According to GPC, the epoxy compound was a mixture containing 78 mole % of component in which n=0, 19 mole % of component in which n=1, and 3 mole % of component in which n=2 or more, wherein the average of n was 0.25.

The obtained epoxy compound was yellow crystallized solid at room temperature so as to have good handling property.

EXAMPLE I-3

EXAMPLE 1-3-A 1050 g of epichlorohydrin and 410 g of 2-propanol were charged into a four-necked flask of 3 liters capacity equipped with a stirrer, a flux cooling pipe and a thermometer. A system was vacuumed and replaced by nitrogen and was kept at a temperature of 40° C. Under the nitrogen atmosphere, 900 g of 28 mass % aqueous solution of 1,4-dihydroanthrahydroquinone sodium salt was added dropwise over 90 minutes. During the addition, temperature was gradually elevated such that the temperature in the system reached 65° C. at the time of completion of the addition. Thereafter, the system was maintained at 65° C. for 30 minutes to discharge water containing by-product salts due to liquid-liquid separation. With maintaining the temperature in the system at 65° C., 32 g of 48.5 mass % aqueous sodium hydroxide solution was added thereto dropwise over 15 minutes and the reaction was continuously achieved for 30 minutes. After completion of the reaction, the reaction mixture was washed with water to remove by-product salts. Further, excess epichlorohydrin and 2-propanol were distilled off under reduced pressure from the product to obtain a crude epoxy resin mixture.

This rough epoxy resin mixture was dissolved in 460 g of methyl isobutyl ketone, and 7 g of 48.5 mass % aqueous sodium hydroxide solution was added thereto to conduct reaction at a temperature of 65° C. for 1 hour. After that, aqueous sodium primary phosphate solution was added to the reaction liquid to neutralize excess sodium hydroxide, followed by water washing to remove by-product salts. After methyl isobutyl ketone was completely removed under increased temperature and reduced pressure, resin matter in melted state was pulled onto a tray and stirred dozen times by a glass stick and, after that, was naturally cooled at room temperature. After a lapse of 2 hours, entire crystallization was experienced. The crystallized matter was taken out, thereby obtaining 290 g of yellow crystallized epoxy compound.

The obtained epoxy compound had an epoxy equivalent of 174 g/eq, hydrolysable chlorine of 390 ppm, and a melt viscosity of 15 m Pa·s at a temperature of 150° C., and a melting point of 106° C. according to DSC. The obtained epoxy compound was solid at room temperature so as to have good handling property.

H-NMR spectrum and IR spectrum of the obtained epoxy compound were substantially the same of the epoxy compound obtained in Example I-1 so that it was confirmed that the obtained epoxy compound was an epoxy compound represented by the aforementioned structural formula (III). According to DSC, the epoxy compound was a mixture containing 84 mole % of component in which n=0, 14 mole % of component in which n=1, and 2 mole % of component in which n=2 or more, wherein the average of n was 0.18.

EXAMPLE I-3-B 100 g of epoxy compound obtained in Example I-3-A was recrystallized by using 100 g of methyl ethyl ketone, thereby obtaining 45 g of recrystallized compound. The obtained recrystallized compound had an epoxy equivalent of 163 g/eq, hydrolysable chlorine of 20 ppm, a melt viscosity of 8 m Pa·s at a temperature of 150° C., and a melting point of 120° C. according to DSC. According to GPC, the recrystallized compound was a mixture containing 97 mole % of component in which n=0 and 2 mole % of component in which n=1 in the aforementioned structural formula (III), wherein the average of n was 0.01.

EXAMPLES I-4 THROUGH I-6

Each of epoxy compounds made in Examples I-1 through I-3 and phenol novolak resin(softening point of 84° C., hydroxyl equivalent of 103 g/eq) or phenol aralkyl resin (softening point of 83° C., hydroxyl equivalent of 175 g/eq) as a curing agent were charged in a glass beaker in predetermined respective amounts and were dissolved and mixed at 120° C. Further, triphenyl phosphine was added as a curing accelerator in a predetermined amount and was mixed well so as to obtain a composition. The composition was molded and was postcured at 175° C. for 7 hours, thereby obtaining a cured product. The compounding ratios of the compositions and properties of the obtained cured products are shown in Table 2.

COMPARATIVE EXAMPLES I-1, I-2

Cured products were made in the same manner as Example I-4 by using bisphenol A type epoxy resin (liquid at ordinary temperature, viscosity of 10 m Pa·s at 150° C.) and tetramethylbiphenol type epoxy resin (melting point of 105° C., viscosity of 15 m Pa·s at 150° C.), respectively, instead of the epoxy compound obtained in Example I-1 with compounding ratios shown in Table 2. The results of measured properties of the obtained cured products are shown in Table 2.

TABLE 2

|  | Example 4 | Example 5 | Example 6 | Comparative Example 1 | Comparative Example 2 |
|---|---|---|---|---|---|
| [Composition] (phr) | | | | | |
| Epoxy compound of Example 1 | 100.0 | | | | |
| Epoxy compound of Example 2 | | 100.0 | | | |

TABLE 2-continued

|  | Example 4 | Example 5 | Example 6 | Comparative Example 1 | Comparative Example 2 |
|---|---|---|---|---|---|
| Epoxy compound of Example 3 |  |  | 100.0 |  |  |
| Bisphenol A type epoxy resin |  |  |  | 100.0 |  |
| Tetramethylbiphenol type epoxy resin |  |  |  |  | 100.0 |
| Phenol novolak resin | 58.5 | 53.1 |  | 55.4 |  |
| Phenol aralkyl resin |  |  | 100.6 |  | 94.1 |
| Triphenyl phosphine | 1.0 | 1.0 | 1.0 | 1.0 | 1.0 |
| [Properties] |  |  |  |  |  |
| Gel time (*1) (seconds) | 60 | 63 | 72 | 70 | 95 |
| Glass transition temperature (*2) (° C.) | 167 | 162 | 145 | 115 | 120 |
| Flexural strength (23° C.) (*3) (kg/mm$^2$) | 16 | 15.8 | 15.2 | 14.7 | 13.3 |
| Flexural modulus (23° C.) (*3) (kg/mm$^2$) | 370 | 361 | 324 | 315 | 274 |
| Flexural strength (250° C.) (*3) (kg/mm$^2$) | 0.34 | 0.31 | 0.25 | 0.12 | 0.11 |
| Flexural modulus (250° C.) (*3) (kg/mm$^2$) | 3.4 | 3.3 | 2.9 | 2.9 | 1.8 |
| Hygroscopic rate (*4) (%) | 0.71 | 0.69 | 0.64 | 0.9 | 0.72 |

(*1) Measured at 175° C. by a hotbench test
(*2) Measured by using TMA
(*3) Tests were conducted according to JIS K6911
(*4) Hygroscopic rate after 72 hours at 85° C. and 85% RH Apparent from the above, the epoxy compound of the present invention is a crystalline resin and solid at ordinary temperature so as to have excellent handling property and, in its melted state, has extremely low viscosity. The results further show that the curable epoxy resin composition prepared by using the epoxy compound is excellent in curing property, and the epoxy compound can provide a cured product having excellent mechanical strength, heat resistance, and moisture resistance.

[Explanation of Epoxy Resin Composition for Semiconductor Encapsulation and Semiconductor Device]

An epoxy compound used for an epoxy resin composition for semiconductor encapsulation of the present invention is the epoxy compound of the first aspect (hereinafter, sometimes referred to as the first epoxy compound) which can be prepared by causing reaction between an anthrahydroquinone compound represented by the aforementioned general formula (II) and epihalohydrin in a known suitable manner.

As discussed above, the anthrahydroquinone compound and anthrahydroquinone alkali metal salt (or its aqueous solution) as the material of the epoxy compound can be prepared in a known suitable manner (JP-S54-122263-A). In addition, since aqueous solution of 1,4-dihydroanthrahydroquinone disodium salt wherein $R^1$-$R^{10}$ are hydrogen atoms in the aforementioned general formula (II) is already widely used in the world for applications as pulping cooking auxiliary agent, aqueous solution of 1,4-dihydroanthrahydroquinone disodium salt may be used without any process.

In view of flame retardancy and low melt viscosity of the epoxy resin composition of the present invention, the epoxy resin is an epoxy compound represented by the aforementioned structural formula (III) or (V) and is composed of a compound (1,4-dihydroanthrahydroquinone) wherein $R^1$-$R^{10}$=hydrogen atoms and $A^1$=$A^2$=hydrogen atoms in the aforementioned general formula (II), a compound (1,4-dihydroanthrahydroquinone disodium salt) wherein $R^1$-$R^{10}$=hydrogen atoms and $A^1$=$A^2$=Na in the aforementioned general formula (II), a compound (2,3-dimethyl-1,4-dihydroanthrahydroquinone) wherein $R^3$, $R^4$=methyl groups, $R^1$, $R^2$, $R^5$-$R^{10}$=hydrogen atoms, and $A^1$=$A^2$=hydrogen atoms, or a compound (2,3-dimethyl-1,4-dihydroanthrahydroquinone disodium salt) wherein $R^3$, $R^4$ methyl groups, $R^1$, $R^2$, $R^5$-$R^{10}$=hydrogen atoms, and $A^1$=$A^2$=Na. The average of n is preferably 0-5, especially preferably 0-2.

The epoxy resin contained in the epoxy resin composition for semiconductor encapsulation of the present invention may be composed only of the first epoxy compound or a combination of the first epoxy compound and one or more of second epoxy compound(s) different from the first epoxy compound. The second epoxy compound prepared separately from the first epoxy compound may be mixed with the first epoxy compound. A compound as the material of the second epoxy compound may be mixed with a compound as the material of the first epoxy compound and the mixture is reacted with epihalohydrin so as to prepare an epoxy resin of the mixture of the both epoxy compounds.

The second epoxy compound may be any of known suitable epoxy compounds and specifically may be an epoxy resin prepared from a polyhydric phenol or a phenolic resin with an epihalohydrin. Examples include epoxy resins prepared from various polyhydric phenols such as bisphenol F, bisphenol AD, bisphenol, tetramethylbiphenol, bis(4-hydroxyphenyl)methane, bis(4-hydroxyphenyl)propane, terpene diphenol, hydroquinone, methylhydroquinone, dibutylhydroquinone, resorcin, methyl resorcin, bisphenol S, thiodiphenol, dihydroxydiphenyl ether, dihydroxynaphthalene, phenol novolak resin, orthocresol novolak resin, bisphenol A novolak resin, dicyclopentadiene phenolic resin, terpene phenolic resin, phenol aralkyl resin, and naphthol novolak resin, or various phenolic compounds such as phenolic resins, obtained by condensation reaction of various phenols and various aldehydes, such as benzaldehyde, hydroxybenzaldehyde, crotonaldehyde, and glyoxal, or phenol denatured xylene resin with an epihalohydrin; epoxy resins prepared from an amine compound with an epihalohydrin, for example, epoxy resins prepared from diaminodiphenylmethane, aminophenol, or xylenediamine with an epihalohydrin; and epoxy resins prepared from carboxylic acids with an epihalohydrin, for example, epoxy resins prepared from an amine compound such as methylhexahydroxyphthalic acid or dimer acid with an epihalohydrin. These epoxy resins may be used in combination.

The mixing proportion between the first epoxy compound and the second epoxy compound to be employed in the present invention is set such that the second epoxy compound is between 0% by mass and 95% by mass in case of the first epoxy compound being between 5% by mass and 100% by mass, preferably that the second epoxy compound is between 0% by mass and 85% by mass in case of the first epoxy compound being between 15% by mass and 100% by mass, more preferably that the second epoxy compound is between 0% by mass and 60% by mass in case of the first epoxy compound being between 40% by mass and 100% by mass. If the mixing proportion of the first epoxy compound is too small, sufficient characteristics of the epoxy resin composition of the present invention can not be provided.

"A phenolic curing agent having two or more phenolic hydroxyl groups per molecule" as an essential components in the epoxy resin composition for semiconductor encapsulation of the present invention may be any one of known suitable curing agents. Examples include various polyhydric phenols, such as bisphenol A, bisphenol F, bisphenol S, thiodiphenol, hydroquinone, resorcin, biphenol, tetramethylbiphenol, dihydroxynaphthalene, and dihydroxydiphenyl ether, phenol novolak resin, cresol novolak resin, bisphenol A novolak resin, naphthol novolak resin; various phenolic resins such as polyhydric phenol resin obtained by condensation reaction of various phenols and various aldehydes such as benzaldehyde, hydroxybenzaldehyde, methylthiobenzaldehyde, crotonaldehyde or glyoxal, phenol aralkyl resin, phenol terpene resin, and dicyclopentadiene phenolic resin; and modified phenol resins obtained by condensation reaction of heavy oils or pitches, phenols, and aldehyde compounds.

In view of low hygroscopicity and flame retardancy of the composition after curing, phenol novolak resin [e.g. the following formula (VI)], phenol aralkyl resin [e.g. the following formulae (VII) and (VIII)], naphthol novolak resin [e.g. the following formula (IX)], and naphthol aralkyl resin [e.g. the following formula (X)] are especially preferable among the aforementioned phenolic curing agents. It should be noted that x designates an integer of 0 or more.

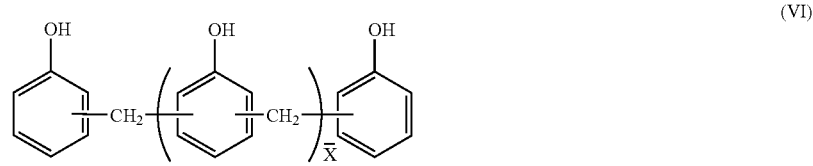

(VI)

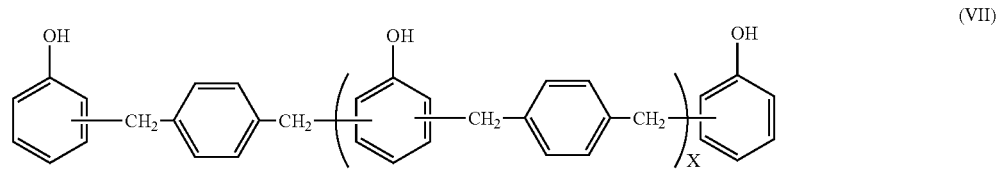

(VII)

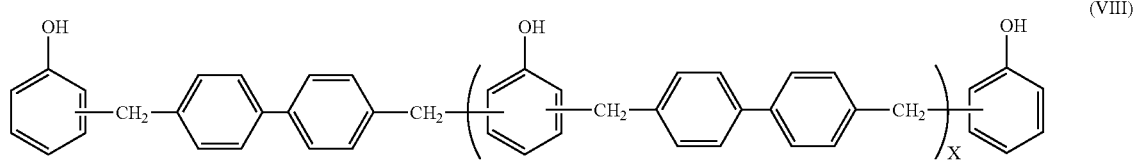

(VIII)

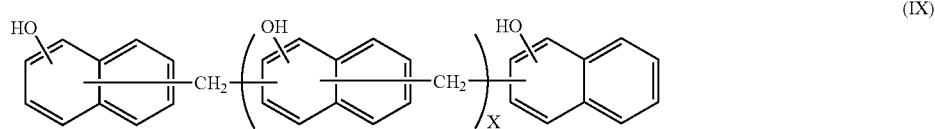

(IX)

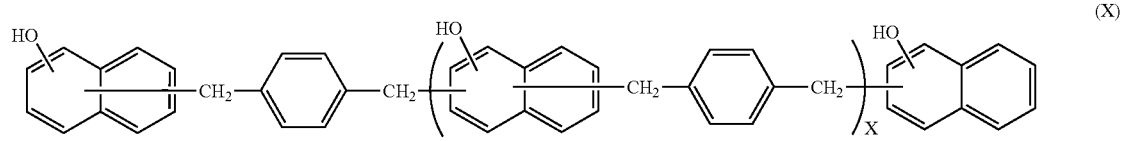

(X)

These phenolic curing agents may be used alone or in combination. These phenolic curing agents of various types are available as commercial items. Examples of phenol aralkyl resin include MEH7800 available from Meiwa Plastic Industries, Ltd. [corresponding to the formula (VII)] and MEH7851 available from Meiwa Plastic Industries, Ltd. [corresponding to the formula (VIII)], examples of naphthol novolak resin include NC-30 available from Gunei Chemical Industry Co., Ltd [corresponding to the formula (IX)], and examples of naphthol aralkyl resin include MEH7810 available from Meiwa Plastic Industries, Ltd. [corresponding to the formula (X)].

The epoxy resin composition for semiconductor of the present invention can also employ a curing agent other than the phenolic curing agent to be mixed with the phenolic curing agent. Examples of the curing agent to be mixed with the phenolic curing agent include anhydrides such as methyltetrahydrophthalic anhydride, hexahydrophthalic anhydride, pyromellitic anhydride and methylnadic acid; amines, such as diethylene triamine, isophorone diamine, diaminodiphenyl methane, diaminodiphenyl sulfone and dicyandiamide; and activated ester compound obtained by converting all or a part of phenolic hydroxyl groups of various phenol compounds specified as examples of the aforementioned phenolic curing agent into ester such as benzoate or acetate.

The respective components of the curing agent may be previously mixed to prepare a mixture curing agent before use. Alternatively, the components of the curing agent may be separately added when components of an epoxy resin composition are mixed for preparing the epoxy resin composition so that all components are then mixed simultaneously. The amount of the curing agent to be used is set that groups reacting with the epoxy groups in the entire curing agent are preferably 0.5-2.0 moles, more preferably 0.7-1.2 moles relative to one mole of epoxy groups in all components of the epoxy resin.

An inorganic filler is compounded in the epoxy resin composition for semiconductor encapsulation of the present invention. Kinds of the inorganic filler are, for example, fused silica, crystalline silica, glass powder, alumina, and calcium carbonate. The shape thereof is a pulverized form or a spherical form. These inorganic fillers are used alone or as mixtures of two kinds or more thereof. Among these, the fused silica and crystalline silica are preferably used.

The amount thereof used is 60-95% by mass of the whole composition. In case of too small amount of the inorganic filler, the hygroscopicity must be large so as to affect the solder crack resistance. In case of too large amount of the inorganic filler, the fluidity during molding must be spoiled.

The particle diameter of the inorganic filler depends on the configuration of the semiconductor device to which the resultant epoxy resin composition is adopted and the characteristics required. However, the average particle diameter is preferably 1-100 μm, more preferably 5-50 μm. To increase the filling ratio for adjusting the expansion coefficient, to adjust the fluidity, and to reduce defective products due to flash during molding, inorganic filler of which average particle diameter is 0.01-1 μm may also be added.

The curing accelerator used in the epoxy resin composition for semiconductor encapsulation of the present invention is a compound that accelerates the curing reaction between epoxy groups in the epoxy resin and hydroxyl groups in the phenolic curing agent. Specific examples include phosphine compounds such as tributyl phosphine, triphenyl phosphine, tris(dimethoxyphenyl)phosphine, tris(hydroxypropyl)phosphine and tris(cyanoethyl)phosphine; phosphonium salts such as tetraphenylphosphonium tetraphenylborate, methyltributylphosphonium tetraphenylborate and methyltricyanoethyl phosphonium tetraphenylborate; triphenylphosphine-benzoquinone adducts; imidazoles such as 2-methyl imidazole, 2-phenyl imidazole, 2-ethyl-4-methyl imidazole, 2-undecyl imidazole, 1-cyanoethyl-2-methyl imidazole, 2,4-dicyano-6-[2-methylimidazolyl-(1)]-ethyl-S-triazine and 2,4-dicyano-6-[2-undecylimidazolyl-(1)]-ethyl-S-triazine; imidazolium salts such as 1-cyanoethyl-2-undecylimidazolium trimellitate, 2-methylimidazolium isocyanurate, 2-ethyl-4-methylimidazolium tetraphenylborate and 2-ethyl-1,4-dimethylimidazolium tetraphenylborate; amines such as 2,4,6-tris(dimethylaminomethyl)phenol, benzyl dimethylamine, tetramethylbutyl guanidine, N-methylpiperazine and 2-dimethylamino-1-pyrroline; ammonium salts such as triethylammonium tetraphenylborate; diazabicyclo compounds such as 1,5-diazabicyclo[5,5,0]-7-undecene, 1,5-diazabicyclo[4,3,0]-5-nonene and 1,4-diazabicyclo[2,2,2]-octane; and tetraphenylborates, phenol salts, phenol novolak salts and 2-ethylhexanoates of these diazabicyclo compounds.

Among these curing accelerators, tertiary amines, phosphine compounds, imidazol compounds, diazabicyclo compounds, and salts thereof are preferable.

These compounds as curing accelerators can be used alone or in mixed state of two or more. The amount of the curing accelerator to be used is 0.1-7% by mass, preferably 0.5-5% by mass, more preferably 0.5-3% by mass relative to the whole epoxy resin of the composition of the present invention. Since the curing accelerator sometimes significantly effects the curing property and storage stability of the resultant composition, the kind and the amount of the used curing accelerator can be adjusted not to spoil the characteristics of the present invention.

If necessary, coupling agent, carbon black, coloring agent, flame retardant, flame retardant aid, mold-releasing agent, ion supplement, stress soothing agent, and the like can be appropriately compounded in the epoxy resin composition for semiconductor encapsulation of the present invention not to spoil characteristics of the composition of the present invention. Though the amount can be changed according to the kind of the semiconductor device to which the resultant epoxy resin composition is adopted and generally is 0.01-3% by mass relative to the whole components.

Examples of the flame retardant include halogen type flame retardants such as brominated epoxy resin and brominated phenolic resin, antimony compounds such as antimony trioxide, phosphorus type flame retardants such as red phosphorus, surface-coated red phosphorus, phosphoric esters and phosphines, nitrogen type flame retardants such as melamine derivatives, inorganic flame retardants such as aluminum hydroxide and magnesium hydroxide, phosphazene flame retardants, and special silicone flame retardants.

Since the cured product of the epoxy resin composition for semiconductor encapsulation of the present invention has excellent flame retardance, the use of such flame retardant, especially, the halogen type flame retardants such as brominated epoxy resin or brominated phenolic resin and antimony compounds such as antimony trioxide which are concerned about environmental safety can be eliminated or very small amount of such flame retardant can be enough. However, since the flame retardance depends on the kinds and the amounts of the respective components of the composition, the respective components are selected and the amounts thereof must be adjusted in order to ensure flame retardance according to V-0 of UL-94 standard or equivalent.

It is required to consider the combination of an epoxy resin and a phenolic curing agent to be used in the epoxy resin composition for semiconductor encapsulation of the present invention in such a manner that the melt viscosity at 150° C. of a mixture in which the epoxy resin and the phenolic curing agent are mixed in equivalent amounts is 10-200 m Pa·s, preferably 20-120 m Pa·s in view of the fluidity of the epoxy resin composition. Melt viscosity lower than 10 m Pa·s is not suitable because defective products due to voids (phenomenon that turbulent flow of composition occurs in a mold during molding and makes a cured product in which air is trapped) are easily produced. Melt viscosity higher than 200 m Pa·s is also not suitable because defective products such as shifts of semiconductor chips and shifts of wires are easily produced. The measurement of the melt viscosity was made with by using a cone-plate rotating viscometer (for example, CV-1D manufactured by Misec Corporation) with conditions that the plate temperature was 150° C., a cone had 5 poises, the rotation speed was 750 rpm, and the sample amount was 0.5 g.

The epoxy resin composition for semiconductor encapsulation of the present invention is made such that the hygroscopic rate of a cured product after heated and cured is from 0.1% to 0.5%. The hygroscopic rate in this application is commonly recognized that the lower the better. However, an extremely large amount of inorganic filler is required to make the hygroscopic rate lower than 0.1%. The production of a product having hygroscopic rate lower than 0.1% is impossible in practice. In case of hygroscopic rate higher than 0.5%, defective products due to solder cracks are frequently produced so that it is ineligible for application of semiconductor encapsulation.

Though the epoxy resin composition for semiconductor encapsulation of the present invention has a characteristic of moisture resistance, the characteristic depends on the kinds and the amounts of the respective components of the composition and additives other than essential components. Therefore, it is required to select the respective components and adjust the amounts thereof not to make hygroscopic rate exceeding 0.5%. The hygroscopic rate is obtained by the following equation:

Hygroscopic rate=[(mass of sample piece after process in a temperature- and moisture-controlled tank at 85° C. and 85% RH for 72 hours−mass of the sample piece before the process)/mass of the sample piece before the process]×100

The method of mixing the essential components and the other components of the epoxy resin composition for semiconductor encapsulation of the present invention is not particularly limited and may be any of methods capable of uniformly dispersing and mixing the components. An example of general methods is a method comprising sufficiently mixing predetermined amounts of components by a mixer or the like, then melting and mixing the mixture by using a mixing roll or a kneader with being heated, if necessary, cooling the melted mixture to solidify it, and pulverizing the solid mixture. The composition after pulverized can be formed to have such size and weight as to satisfy molding conditions and be in form of tablets by a tableting machine.

Since the epoxy resin composition for semiconductor encapsulation of the present invention has excellent handling property because it is solid at ordinary temperature and has low blocking property, the epoxy resin composition also has good pulverizing property and tableting property.

The semiconductor device of which semiconductor elements are encapsulated of the present invention can be produced by encapsulating semiconductor chips with the aforementioned composition. Semiconductor chips to be encapsulated are not particularly limited and may be integrated circuits, large-scale integrated circuits, transistors, thyristors, and diodes. The configuration of semiconductor package is also not particularly limited. An encapsulating method is generally low-pressure transfer molding and may be injection molding, compression molding, cast molding, or potting. Semiconductor device encapsulated by the transfer molding is installed to electronic equipments or the like directly or after completely cured at a temperature of 80-200° C. taking from 15 seconds to 10 hours.

As described in the above, the epoxy resin composition for semiconductor encapsulation of the present invention and the semiconductor device encapsulated by using the epoxy resin composition have superior flame retardance without adding halogen compound and/or antimony compound, which are concerned about environmental safety, and have excellent solder crack resistance.

Hereinafter, examples of the epoxy resin composition for semiconductor encapsulation of the present invention and the semiconductor device will be described in detail with experiment examples. However, the present invention is not limited to these examples without departing from the scope of the invention.

EXAMPLES

As shown in Table 3, each example was made by charging an epoxy resin and a curing agent in equivalent amounts wherein the epoxy resin was each of epoxy compounds prepared in the aforementioned Examples I-1 and I-2, a commercially available orthocresol novolak type epoxy resin, a brominated epoxy resin, and a biphenyl type epoxy resin and the curing agent was one of phenol novolak resin, phenol aralkyl resin, naphthol novolak resin, and naphtol aralkyl resin, and heating to melt and mixing them. The melt viscosity at 150° C. of each example was measured. The results are shown in Table 3.

TABLE 3

| | | No. | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | |
| Composition | Proportion of First Epoxy Compound (parts by mass) | (III) 100 | (III) 100 | (III) 100 | (III) 100 | (V) 100 | (III) 20 | (III) 50 | (V) 80 | | | | |
| | Proportion of Other Epoxy Compound (parts by mass) | | | | | | E-1 80 | E-2 50 | E-3 20 | E-3 100 | E-1 100 | E-1 100 | E-4 10 |
| | Proportion of Phenolic Curing Agent (parts by mass) | P-1 59 | P-2 99 | P-3 113 | P-4 72 | P-5 108 | P-2 95 | P-2 101 | P-1 52 | P-1 49 | P-2 94 | P-2 99 | |
| | Melt Viscosity(*) (m Pa · s) | 41 | 63 | 52 | 42 | 69 | 65 | 112 | 62 | 262 | 64 | 153 | |
| | Remarks | | | | | Examples | | | | | Comparative Examples | | |

(III) Epoxy compound represented by the structural formula (III) prepared in Example I-1
(V) Epoxy compound represented by the structural formula (V) prepared in Example I-2
E-1 Biphenyl-type epoxy resin (Epikote YX4000, a brand name of Japan Epoxy Resins Co., Ltd., Epoxy equivalent: 186 g/eq)
E-2 Triphenylmethane-type epoxy resin (Epikote 1032H60, a brand name of Japan Epoxy Resins Co., Ltd., Epoxy equivalent: 170 g/eq)
E-3 Cresol novolak-type epoxy resin (Epikote 180S62, a brand name of Japan Epoxy Resins Co., Ltd., Epoxy equivalent: 210 g/eq)
E-4 Brominated epoxy resin (BREN-S, a brand name of Nippon Kayaku Co., Ltd., Epoxy equivalent: 385 g/eq, bromine content: 48%)
P-1 Phenol novolak resin (Resitop PSM4261, a brand name of Gunei Chemical Industry Co., Ltd., Hydroxyl group equivalent: 103 g/eq, Softening point: 85° C.)
P-2 Phenol aralkyl resin (MEH-7800S, a brand name of Meiwa Plastic Industries, Ltd., Hydroxyl group equivalent: 175 g/eq, Softening point: 75° C.)
P-3 Phenol aralkyl resin (MEH-7851, a brand name of Meiwa Plastic Industries, Ltd., Hydroxyl group equivalent: 198 g/eq, Softening point: 73° C.)
P-4 Naphtol novolak resin (NC-30, a brand name of Gunei Chemical Industry Co., Ltd., Hydroxyl group equivalent: 126 g/eq, Softening point 83° C.)
P-5 Naphtol aralkyl resin (MEH-7810, a brand name of Meiwa Plastic Industries, Ltd., Hydroxyl group equivalent: 210 g/eq, Softening point: 86° C.)

Measurement Condition
Cone-plate type viscometer (CV-1D manufactured by Misec Corporation)
Plate temperature: 150° C., rotation speed: 750 rpm, cone: 5 poises Measurement Procedures
1) 0.5 g of a sample is left on a plate at rest for 1 minute and is completely melted.
2) A cone is brought in contact with the melted sample and, as the plate temperature becomes stable at 150° C., is rotated at a predetermined rotational speed. After a lapse of 10 seconds, the viscosity is measured.

Examples II-1 through II-8 and Comparative Examples II-1 through II-3

Each epoxy resin composition for semiconductor encapsulation was made in the same manner as each of Experiment Examples No. 1 through No. 11 except further using spherical melted silica powder (average particle diameter: 28 µm) as an inorganic filler, triphenyl phosphine as a curing accelerator, brominated phenol novolak epoxy esin as a flame retardant, antimony trioxide as a flame retardant aid, carnauba wax as a mold release agent, and epoxy silane as a silane coupling agent, with proportions of the respective components shown in Table 4.

The components were melted and mixed by using a mixing roll at a temperature of 70-130° C. for 5 minutes. Thus obtained melted mixture was pulled onto a sheet and was solidified with cooling at a temperature of 20-25° C. After that, the solidified mixture was pulverized so as to obtain a molding material.

The molding material was molded by using a low pressure transfer molding machine at a mold temperature of 175° C. and for a molding time period of 90 seconds, thereby obtaining a sample piece and a 160-pin TQFP type resin encapsulated semiconductor device. The obtained sample piece and semiconductor device are postcured at 175° C. for 5 hours.

In order to evaluate the curing property and the fluidity as indicators of the moldability of each molding material, each molding material was measured for hardness just after removed from the mold and spiral flow. In addition, each molding material after postcured was tested for glass transition temperature, hygroscopic rate, and flame retardance. Moreover, each resin encapsulated semiconductor device was tested for solder crack resistance after absorbing moisture. These results are shown in Table 4.

TABLE 4

| | | | Examples | | | | | |
|---|---|---|---|---|---|---|---|---|
| | | Example | II-1 | II-2 | II-3 | II-4 | II-5 | II-6 |
| Components of Epoxy Resin Composition | | Proportion of First Epoxy Compound | (III) 100 | (III) 100 | (III) 100 | (III) 100 | (V) 100 | (III) 20 |
| | | Proportion of Other Epoxy Compound | | | | | | E-1 80 |
| | | Proportion of Phenolic Curing Agent | P-1 59 | P-2 99 | P-3 113 | P-4 72 | P-5 108 | P-2 95 |
| | | Silica Powder | 1074 | 1348 | 1436 | 1162 | 1407 | 1319 |
| | | Triphenyl Phosphine | 1.5 | 1.5 | 1.5 | 1.5 | 1.5 | 1.5 |
| | | Antimony Trioxide | 0 | 0 | 0 | 0 | 0 | 0 |
| | | Carnauba Wax | 1 | 1 | 1 | 1 | 1 | 1 |
| | | Carbon Black | 0.5 | 0.5 | 0.5 | 0.5 | 0.5 | 0.5 |
| | | Silane Coupling Agent (Note 1) | 1 | 1 | 1 | 1 | 1 | 1 |
| Test Results | Curing Properties | Spiral Flow (cm) | 78 | 85 | 89 | 81 | 79 | 85 |
| | | Hardness just after removed from mold (Note 2) | 85 | 80 | 75 | 85 | 74 | 71 |
| | | Hygroscopic Rate (%) (Note 3) | 0.23 | 0.21 | 0.18 | 0.21 | 0.19 | 0.25 |
| | | Glass Transition Temperature (Note 4) | 145 | 125 | 120 | 155 | 128 | 120 |
| | | Solder Crack Resistance (Note 5) | 0/16 | 0/16 | 0/16 | 0/16 | 0/16 | 0/16 |
| | | Flame Retardance | V-0 | V-0 | V-0 | V-0 | V-0 | V-0 |

TABLE 4-continued

|  | Example | Examples | | Comparative Examples | | |
| --- | --- | --- | --- | --- | --- | --- |
|  |  | II-7 | II-8 | I-1 | I-2 | I-3 |
| Components of Epoxy Resin Composition | Proportion of First Epoxy Compound | (III) 50 | (V) 80 |  |  |  |
|  | Proportion of Other Epoxy Compound | E-2 50 | E-3 20 | E-3 100 | E-1 100 | E-1 100 E-4 10 |
|  | Proportion of Phenolic Curing Agent | P-2 101 | P-1 52 | P-1 49 | P-2 94 | P-2 99 |
|  | Silica Powder | 1360 | 1033 | 1011 | 1312 | 1496 |
|  | Triphenyl Phosphine | 1.5 | 1.5 | 1.5 | 1.5 | 1.5 |
|  | Antimony Trioxide | 0 | 0 | 0 | 0 | 12 |
|  | Carnauba Wax | 1 | 1 | 1 | 1 | 1 |
|  | Carbon Black | 0.5 | 0.5 | 0.5 | 0.5 | 0.5 |
|  | Silane Coupling Agent (Note 1) | 1 | 1 | 1 | 1 | 1 |
| Test Results | Curing Properties | Spiral Flow (cm) | 70 | 70 | 45 | 90 | 85 |
|  |  | Hardness just after removed from mold (Note 2) | 86 | 83 | 87 | 65 | 70 |
|  |  | Hygroscopic Rate (%) (Note 3) | 0.28 | 0.27 | 0.41 | 0.30 | 0.35 |
|  |  | Glass Transition Temperature (Note 4) | 175 | 148 | 150 | 115 | 118 |
|  |  | Solder Crack Resistance (Note 5) | 0/16 | 0/16 | 16/16 | 9/16 | 11/16 |
|  |  | Flame Retardance | V-0 | V-0 | Burnout | Burnout | V-0 |

The proportions in the table are indicated as parts by mass.
(III) Epoxy compound represented by the structural formula (III) prepared in Example I-1
(V) Epoxy compound represented by the structural formula (V) prepared in Example I-2
E-1 Biphenyl-type epoxy resin (Epikote YX4000, a brand name of Japan Epoxy Resins Co., Ltd., Epoxy equivalent: 186 g/eq)
E-2 Triphenylmethane-type epoxy resin (Epikote 1032H60, a brand name of Japan Epoxy Resins Co., Ltd., Epoxy equivalent: 170 g/eq)
E-3 Cresol novolak-type epoxy resin (Epikote 180S62, a brand name of Japan Epoxy Resins Co., Ltd., Epoxy equivalent: 210 g/eq)
E-4 Brominated epoxy resin (BREN-S, a brand name of Nippon Kayaku Co., Ltd., Epoxy equivalent: 385 g/eq, bromine content: 48%)
P-1 Phenol novolak resin (Resitop PSM426, a brand name of Gunei Chemical Industry Co., Ltd., Hydroxyl group equivalent: 103 g/eq, Softening point: 85° C.)
P-2 Phenol aralkyl resin (MEH-7800S, a brand name of Meiwa Plastic Industries, Ltd., Hydroxyl group equivalent: 175 g/eq, Softening point: 75° C.)
P-3 Phenol aralkyl resin (MEH-7851, a brand name of Meiwa Plastic Industries, Ltd., Hydroxyl group equivalent: 198 g/eq, Softening point: 73° C.)
P-4 Naphtol novolak resin (NC-30, a brand name of Gunei Chemical Industry Co., Ltd., Hydroxyl group equivalent: 126 g/eq, Softening point 83° C.)
P-5 Naphtol aralkyl resin (MEH-7810, a brand name of Meiwa Plastic Industries, Ltd., Hydroxyl group equivalent: 210 g/eq, Softening point: 86° C.)
Note 1: Epoxy silane (KBM-403, a brand name of Shin-Etsu Chemical Co., Ltd.)
Note 2: Value of ASTM Shore D
Note 3: Hygroscopic rate after 75 hours at 85° C. and 85% RH
Note 4: Measured by TMA method Note 5: Sixteen 160-pin TQFPs were left at 85° C. and 85% RH for 72 hours so that the TQFPs absorbed moisture. After that, these were soaked in a solder bath at 260° C. for 10 seconds. Number of cracks was counted.
Note 6: UL94

As indicated in Table 4, as compared to compositions of Comparative Examples II-1 through II-3, compositions of Examples II-1 through II-8 are excellent in flame retardance without containing halogen compound (brominated phenol novolak epoxy resin) and antimony compound (antimony trioxide) as a flame retardant component, as well as low viscosity, excellent fluidity, and low hygroscopicity. In addition, the semiconductor devices encapsulated using these compositions have excellent solder crack resistance.

What is claimed is:
1. A method of preparing an epoxy compound having a following general formula (I):

General Formula (I)

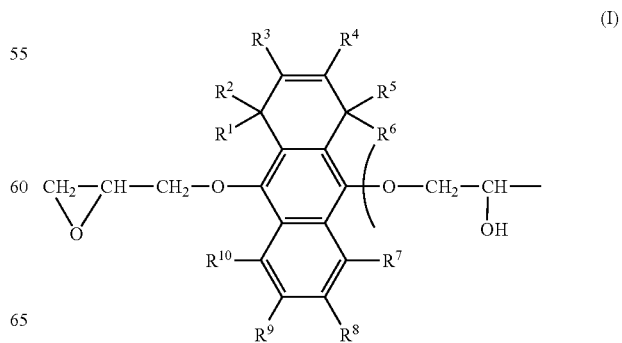

-continued

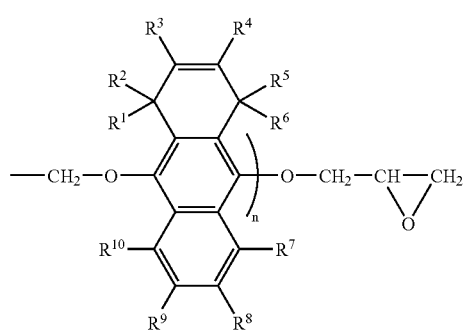

wherein $R^1$-$R^{10}$ each represent hydrogen atom or alkyl group having 1-6 carbon atoms, and n represents an integer of 0 or more, said method comprising the step of reacting an anthrahydroquinone compound having a following general formula (II) with epihalohydrin:

General Formula (II)

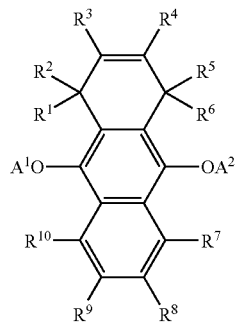

(II)

wherein $A^1$, $A^2$ each represent hydrogen atom or alkali metal atom, $R^1$-$R^{10}$ each represent hydrogen atom or alkyl group having 1-6 carbon atoms.

2. A method of preparing an epoxy compound as claimed in claim 1, wherein $R^1$-$R^{10}$ in the general formula (II) are hydrogen atoms.

3. A method of preparing an epoxy compound as claimed in claim 1, wherein $R^3$, $R^4$ are methyl groups and $R^1$, $R^2$, $R^5$-$R^{10}$ are hydrogen atoms in the general formula (II).

4. A method of preparing an epoxy compound as claimed in claim 1, wherein, reaction between the anthrahydroquinone compound in which $A^1$, $A^2$ are alkali metals in the general formula (II) and the epihalohydrin for preparing an epoxy compound is conducted by supplying an aqueous solution of anthrahydroquinone alkali metal salt into a reaction system.

5. A method of preparing an epoxy compound as claimed in claim 4, wherein concentration of anthrahydroquinone alkali metal salt in the aqueous solution of anthrahydroquinone alkali metal salt to be reacted with epihalohydrin is 5-50% by weight.

6. A method of preparing an epoxy compound as claimed in claim 1, wherein 4-40 moles of epihalohydrin is reacted per one mole of the anthrahydroquinone compound.

7. A method of preparing an epoxy compound as claimed in claim 1, wherein 4-40 moles of epihalohydrin and 1.8-5 moles of alkali metal hydroxide are reacted per one mole of the anthrahydroquinone compound in which $A^1$, $A^2$ are hydrogen in the general formula (II).

* * * * *